US011754572B2

(12) United States Patent
Kostrzewa et al.

(10) Patent No.: US 11,754,572 B2
(45) Date of Patent: Sep. 12, 2023

(54) MASS SPECTROPHOTOMETRIC DETECTION OF MICROBES

(76) Inventors: Markus Kostrzewa, Lilienthal (DE); Jochen Franzen, Bremen (DE)

( * ) Notice: Subject to any disclaimer, the term of this patent is extended or adjusted under 35 U.S.C. 154(b) by 0 days.

(21) Appl. No.: 13/102,212

(22) Filed: May 6, 2011

(65) Prior Publication Data

US 2011/0275113 A1  Nov. 10, 2011

(30) Foreign Application Priority Data

May 7, 2010 (DE) ............... 10 2010 019 870.6

(51) Int. Cl.
C12Q 1/04 (2006.01)
G01N 33/68 (2006.01)
G01N 33/569 (2006.01)

(52) U.S. Cl.
CPC ....... G01N 33/6851 (2013.01); G01N 33/569 (2013.01)

(58) Field of Classification Search
CPC .. G01N 33/6851; G01N 33/569; G01N 33/48; G01N 33/554; G01N 33/68; G06F 19/00
USPC ..... 702/19, 27, 28; 435/6.13, 7.31, 7.32, 29, 435/34
See application file for complete search history.

(56) References Cited

U.S. PATENT DOCUMENTS

| | | | |
|---|---|---|---|
| 7,391,017 | B2 | 6/2008 | Kostrzewa et al. |
| 8,293,496 | B2 | 10/2012 | Govorun et al. |
| 2002/0138210 | A1* | 9/2002 | Wilkes et al. ............ 702/28 |
| 2005/0040325 | A1 | 2/2005 | Gonin |
| 2006/0177824 | A1 | 8/2006 | Procop |
| 2008/0286757 | A1 | 11/2008 | Gaisford et al. |
| 2009/0206247 | A1 | 8/2009 | Holle |
| 2010/0248298 | A1 | 9/2010 | Kostrzewa et al. |
| 2010/0255527 | A1 | 10/2010 | Weller |

FOREIGN PATENT DOCUMENTS

| | | |
|---|---|---|
| DE | 102005002672 | 7/2006 |
| WO | 2010089569 | 8/2010 |
| WO | WO 2010089569 A1 * | 8/2010 |

OTHER PUBLICATIONS

Guo et al., Interaction of bacteria and ion-exchange particles and its potential in separation for matrix-assisted laser desorption/ionization mass spectrometric identification of bacteria in water- Rapid Communications in Mass Spectrometry, Dec. 30, 2009, vol. 23, pp. 3983-3993.*

MALDI-MSI Interest group, Overview of Commercial MALDI-MS, Feb. 15, 2009, http://web.archive.org/web/20090215014410/http://maldi-msi.org/index.php?option=com_content&view=article&id=25&Itemid=50.*

Shroff et al, Nonuniform distribution of glucosinolates in *Arabidopsis thaliana* leaves has important consequences for plant defense, PNAS, Apr. 22, 2008, vol. 105, pp. 6196-6201.*

Nye et al., An evaluation of the performance of XLD, DCA, MLCB, and ABC agars as direct plating media for the isolation of *Salmonella enterica* from faeces, Journal of Clinical Pathology, 2002, vol. 55, pp. 286-288.*

Holle et al, Optimizing UV laser focus profiles for improved MALDI performance, Journal of Mass Spectrometry, May 22, 2006, vol. 41, pp. 705-716.*

Sauer et al., Mass spectrometry tools for the classification and identification of bacteria, Nature Reviews Microbiology, Jan. 2010, vol. 8, pp. 74-82.*

Walker et al, Intact cell mass spectrometry (ICMS) used to type methicillin-resistant *Staphylococcus aureus*: media effects and interlaboratory reproducibility, Journal of Microbiological Methods, 2002, vol. 48, pp. 117-126.*

Moats, W. A., Comparison of Four Agar Plating Media with and Without Added Novobiocin for Isolation of *Salmonellae* from Beef and Deboned Poultry Meat, Applied and Environmental Microbiology, 1978, vol. 36, pp. 747-751.*

Seibold et al., Identification of Francisella tularensis by Whole-Cell Matrix-Assisted Laser Desorption Ionization-Time of Flight Mass Spectrometry: Fast, Reliable, Robust, and Cost-Effective Differentiation on Species and Subspecies Levels, Journal of Clinical Microbiology, 2010, vol. 48, pp. 1061-1069.*

MALDI Biotyper Microorganism Identification and Classification, Bruker Daltonics, 2008, accessed Jun. 2, 2014, http://www.mte-bg.com/~mtebgcom/files/products/products_702.pdf.*

Wahl et al., Analysis of Microbial Mixtures by Matrix-Assisted Laser Desorption/Ionization Time-of-Flight Mass Spectrometry, Analytical Chemistry, 2002, vol. 74, pp. 6191-6199.*

Barbuddhe et al., Rapid Identification and Typing of Listeria Species by Matrix-Assisted Laser Desorption Ionization-Time of Flight Mass Spectrometry, Applied and Environmental Microbiology, 2008, vol. 74, pp. 5402-5407.*

Pantosti et al. 2009. What is MRSA? Series "MRSA and the Pulmonologist" Edited by M. Woodhead and A. Torres No. 1 in this Series. European Respiratory Journal, vol. 34, pp. 1190-1196.*

Williams et al. 2003. Experimental Factors Affecting the Quality and Reproducibility of MALDI TOF Mass Spectra Obtained from Whole Bacteria Cells. Journal of the American Society for Mass Spectrometry. vol. 14, pp. 342-351.*

Fang et al., Use of Cefoxitin-Based Selective Broth for Improved Detection of Methicillin-Resistant *Staphylococcus aureus*, Journal of Clinical Microbiology, Feb. 2006, p. 592-594.*

(Continued)

*Primary Examiner* — Satyendra K Singh

(74) *Attorney, Agent, or Firm* — BENOIT & COTE, INC.

(57) ABSTRACT

A method of detecting specified target microbes in different types of sample uses only one to two cultivation steps for the enrichment of the target microbes from the sample, preferably in selective culture media, combined with a mass spectrometric detection method that identifies the target microbes in mixtures with other microbes even if the target microbes account for only a small proportion of the mixture. The sample may be a food sample, a sample from bodies of water used for bathing, a soil sample, a swabbed sample, a stool sample, an impactor sample with collected aerosol particles, amongst many others. The detection method is several days faster than standard methods and less expensive.

17 Claims, 1 Drawing Sheet

(56) References Cited

OTHER PUBLICATIONS

Voyager-DE, Voyager™ Biospectrometry™ Workstation With Delayed Extraction® Technology, User Guide, Applied Biosystems, 2001.*

Na et al., "Whole-cell matrix-assisted laser desorption/ionization time-of-flight mass spectrometry for rapid identification of bacteria cultured in liquid media", Science China Life Sciences, vol. 54, No. 1, Jan. 2011, p. 48-53.

He et al., "Mass Spectrometry Biotyper System Identifies Enteric Bacterial Pathogens Directly from Colonies Grown on Selective Stool Culture Media", Journal of Clinical Microbiology, vol. 48, No. 11, Nov. 2010, p. 3888-3892.

Christner et al., "Rapid Identification of Bacteria from Positive Blood Culture Bottles by Use of Matrix-Assisted Laser Desorption-Ionization Time of Flight Mass Spectrometry Fingerprinting", Journal of Clinical Microbiology, vol. 48, No. 5, May 2010, p. 1584-1591.

Wenzel et al., "Analysis of mixed cultures of microorganisms using MALDI-TOF mass spectrometry", International Journal of Medical Microbiology, vol. 229, 2009, p. 5, abstract DVP22.

MALDI Biotyper 2.0 User Manual, Version 2.0 SR1, Oct. 2008.

Hoile et al. Optimizing UV Laser Focus Profiles for Improved MALDI Performance, Journal of Mass Spectrometry, vol. 41, 2006, No. 6, pp. 705-716.

Office action for DE102010019870.6 dated Sep. 5, 2018.

* cited by examiner

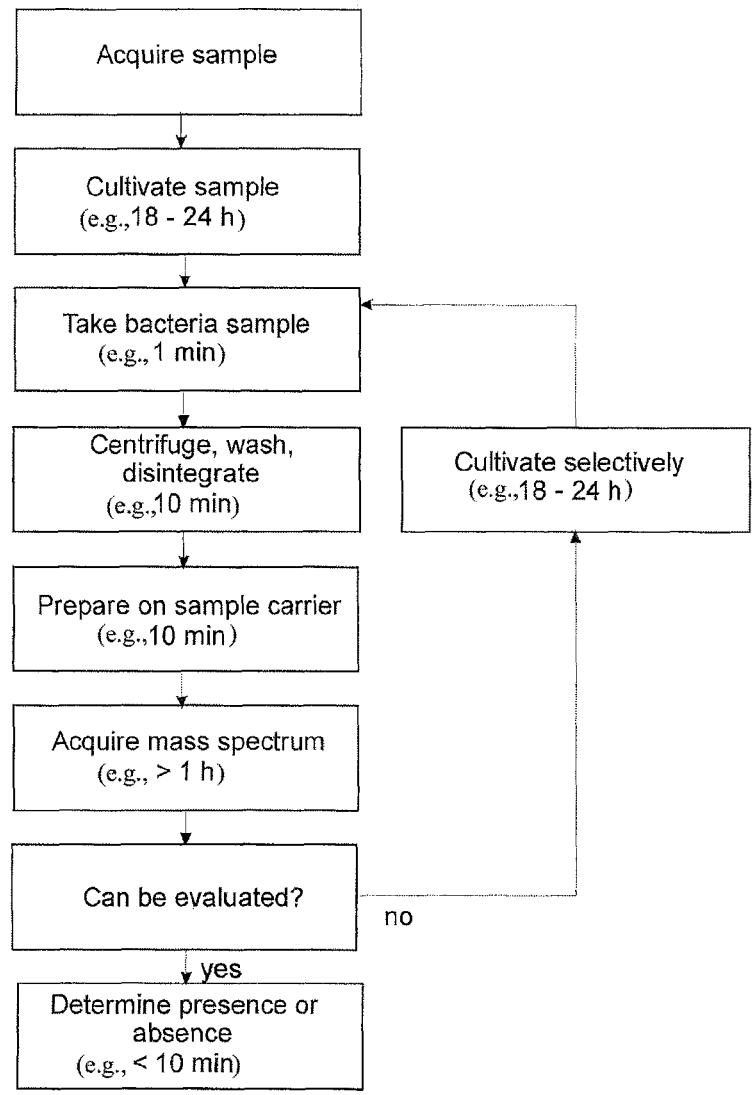

MASS SPECTROPHOTOMETRIC DETECTION OF MICROBES

PRIORITY INFORMATION

This patent application claims priority from German Patent Application 10 2010 019 870.6 filed on May 7, 2010, which is hereby incorporated by reference.

FIELD OF THE INVENTION

The invention relates to the field of mass spectrometry, and in particular to the detection of specified target microbes in different types of sample using a mass spectrometer.

BACKGROUND OF THE INVENTION

The term "microbes" here shall denote all microorganisms such as bacteria, unicellular algae, unicellular fungi or protozoae.

The term "microbe detection" here denotes a method to determine whether a certain species of microbe, called "target microbes", are present in a sample or not. In microbiology, this microbe detection is sometimes also called "qualitative microbe analysis", but this can lead to misunderstandings because it may imply a determination of the identity of unknown microbes. In microbiology, it is usually necessary to follow up any microbe detection with a definite identification of a suspect colony, after corresponding multiplication and isolation of the microbes by cultivation. With mass spectrometric microbe detection, however, the identification occurs automatically.

The detection of microbes, particularly of pathogenic microbes, is important in many areas. Microbe detections must be used wherever it is suspected that certain pathogenic or toxic species of microbe may be present, be it in the monitoring of food, bodies of water used for bathing, the air in operating rooms, water from showers in hotels, cleanliness of sanitary facilities by swabbed samples and many more. A large number of microbe detections arise in the clinical field; for example, stool samples have to be examined when *Salmonella* is suspected.

Microbiological detection methods for microbes generally include an initial, non-selective cultivation step, a second, selective cultivation step, both in liquid cultivation media, a further cultivation on a selective agar plate, and an identification (or confirmation of the suspicion) of a suspect colony, often with the aid of "API tests", but also by dye tests, oxidase tests, catalase tests, indole tests, or other biochemical or serological identification methods. Since the cultivation steps alone take one day each, the total time is at least three days. The detection methods involve a lot of work and are difficult to carry out with a large number of samples simultaneously.

The description below of the detection of *Salmonella* in food services is presented as an example for a standardized detection method. *Salmonella* is a genus of bacteria that belongs to the family of Enterobacteriaceae and is closely related to the *Escherichia* genus. According to the latest consensus, only two species belong to the *Salmonella* genus, namely *S. enterica* and *S. bongori*, the former being subdivided into six sub-species with 2500 serovars nowadays. Most of the *Salmonella* species are pathogenic for humans and animals and may cause mild, but often severe, typhoidal or paratyphoidal bowel infections. They can survive for prolonged periods of time outside the human or animal organism (e.g., in dried feces demonstrably for 2.5 years), but are destroyed at 55° Celsius in one hour, at 60° Celsius in half an hour.

A standard method for detecting *Salmonella* in food is described in § 64 "Collection of Official Analytical Methods (ASU) according to German Food Law (LFGB)" with the designation L 00.00-20. The detection procedure involves transferring 25 grams of the food under investigation to 225 milliliters of a non-selective pre-enrichment broth (buffered peptone water) in order to reactivate and, where necessary, multiply any *Salmonella* present. After incubating for 18 hours at 37° Celsius, two main enrichment cultures are started from the pre-enrichment culture. The main enrichment cultures contain selective media (Müller-Kauffmann Tetrathionate Broth (MKTTn) and Rappaport-Vassiliadis Broth (RVS)) and are inoculated with 0.1 to 1 milliliter of pre-enrichment culture, depending on the broth. MKTTn cultures are incubated at 37° Celsius and RVS cultures at 41.5° Celsius for 24 hours. A smear from each of these main enrichment cultures is made on an XLD agar and a second selective agar (a BPLS or Rambach agar, for example). After incubating the plates for 24 hours at 37° Celsius, they are then examined for colonies of *Salmonella*. If no suspect colonies have grown, the result is negative for *Salmonella*. To further characterize suspect colonies, five colonies are sub-cultivated on non-selective CASO agar (24 hours, 37° Celsius). *Salmonella* is then detected using either "API tests" or latex agglutination. Characterization using "API tests" requires a further 24-hour incubation of the germs at 37° Celsius. This standard method for *Salmonella* in food takes four to five days.

Detection methods from molecular biology which have major advantages over these conventional methods have been known for a number of years. In the food sector, a method of identifying many microorganisms by DNA analysis after a polymerase chain reaction amplification (PCR) is disclosed in U.S. Published Patent Application US 2006 177 824 A1. In contrast to the standard methods of cultivation, this method can provide a result after only one to two days and thus saves valuable time. Its disadvantage includes in the relatively high cost per culture, taking into account the fact that food inspections usually involve many samples each time (sometimes several hundred). Furthermore, PCR is prone to interference, depending on the sample. Extensive positive and negative controls have to be carried out to validate the results.

A further method from molecular biology, but one which so far has almost only been used for the identification of unknown microbes from clean isolates, is based on a mass spectrometric analysis of microbe-specific molecular cell components, predominantly proteins. This method is superior to the conventional microbiological identification methods in terms of specificity (true-negative rate), sensitivity (true-positive rate) and other error rates, and particularly in terms of cost and analytical speed.

The process of generating mass spectra of the components of the microbes to be identified usually starts with a cleanly isolated colony on a solid, usually gelatinous, nutrient medium or a centrifuge sediment (pellet) from a liquid nutrient medium. A small swab, such as a wooden tooth pick, is used to transfer a tiny quantity of microbes from the selected colony or sediment to the mass spectrometric sample support. An acidified solution of a conventional matrix substance is then sprinkled onto this sample, the matrix substance being used for a subsequent ionization of the microbe components by matrix-assisted laser desorption (MALDI). The acid of the matrix solution attacks the cell walls and weakens them; the organic solvent penetrates the microbial cells, causes them to burst by osmotic pressure, and releases the soluble proteins. The sample is then dried by evaporating the solvent, which causes the dissolved matrix material to crystallize. The soluble proteins are thus incorporated into the matrix crystals.

Instead of transferring whole microbes by swabs, the microbes cleaned by washing and centrifuging can also be digested in vitro, in a centrifuge tube, for example, where strong acids can be used that destroy even hard microbial cell walls. Centrifuging separates the insoluble components such as cell walls so that they can no longer interfere with the mass spectrometric analysis. Around one microliter of the supernatant digestion liquid is then applied to the sample support and dried there. The preparation of the sample under analysis is completed on the sample support by coating it with a suitable matrix solution and drying it again, thus incorporating proteins into the matrix crystals. These sample preparations of the digests produce mass spectra that are practically identical to those of the usual preparation on sample supports, but are cleaner; they exhibit less interfering background and are therefore better suited to detect the target microbes, also in mixtures with other microbes.

The sample preparations dried on sample supports, i.e., the matrix crystals with the embedded protein molecules, are bombarded with pulsed UV laser light in a mass spectrometer, thus creating ions of the protein molecules in every laser light pulse. These ions can then be measured, separated according to their mass, in the mass spectrometer. It is preferable to use MALDI time-of-flight mass spectrometers. Several types of crystalline organic acids can be used as matrix substances, among them HCCA (α-cyano-4-hydroxycinnamic acid).

The mass spectra of the microbe proteins are scanned in the linear mode of these time-of-flight mass spectrometers, i.e., without using an energy-focusing reflector, because this mode gives a particularly high detection sensitivity, even though mass resolution and mass accuracy of spectra from time-of-flight mass spectrometers in reflector mode is considerably better. Non-reproducible accelerations during the desorption and ionization processes for the generation of the ions mean that the masses of the individual mass signals shift sometimes. For this reason only small series of individual mass spectra are acquired, summed, and the resulting small series sum spectrum is assessed for quality, particularly for a good mass resolution. Small series of unsatisfactory quality are rejected, those of satisfactory quality are added together to form the sum mass spectrum. In order to correct shifts in the mass scales of the small series of spectra with respect to each other, an adjustment method can be used which was described in U.S. Pat. No. 7,391,017 B2. The method adjusts the mass scales with respect to each other before the small series of spectra are added together to form a sum mass spectrum, which is then used as a reference spectrum or sample spectrum. The mass scales of sample and reference spectra can also be adjusted with respect to each other by this mass scale adjustment program. This means that smaller mass tolerance intervals can be used to determine matching mass signals during the similarity analysis, which is crucial for a good identification, even if it requires some computing time.

The mass spectrum of a microbial isolate is the frequency profile of the mass values of the ions. The ions are predominantly protein ions. The mass spectra are usually acquired in the mass range from 2,000 to 20,000 daltons; the most useful information for identifications is found in the mass range from around 3,000 daltons to 15,000 daltons; the reference mass spectra are therefore usually only stored in this mass range.

Each laser light pulse produces an individual mass spectrum, which is measured in less than 100 microseconds but contains the signals of only a few hundred to a few thousand ions. In order to obtain more reliable and less noisy mass spectra, a few hundred to a few thousands of these individual mass spectra, combined into small series of spectra each comprising 20 to 50 mass spectra, as described above, are added together to form a sum mass spectrum. The small series of spectra here can preferably originate from different parts of the sample preparation or even from different sample preparations. The term "mass spectrum of a microbe", or more simply "microbe spectrum", shall always denote this sum mass spectrum. The acquisition of such a microbe spectrum takes only a few seconds due to the high laser bombardment rates (currently up to two kilohertz). A sample support plate with 48 or even 384 sample preparations can be automatically measured in less than half an hour.

The protein profile represented by each of these microbe spectra is characteristic of the species of microbe in question because each species produces its own, genetically predetermined proteins, each having their own characteristic mass. The abundances of the individual proteins in the microbes, in as much as they can be measured mass spectrometrically, are also genetically predetermined to a large extent because their production is controlled by other proteins, and they depend only slightly on the nutrient medium or the degree of maturity of the colony, as long as no spores form. The protein profiles are characteristic of the microbes in rather the same way that fingerprints are characteristic of humans. This makes it possible to identify the microbes by a similarity analysis with reference spectra from a reference library.

The spectra acquired are evaluated with programs provided by the manufacturers of the mass spectrometers together with the instrument. These programs are based on similarity analyses between a measured microbe spectrum and reference mass spectra from specially validated spectral libraries. This is done by calculating a similarity index score for each reference spectrum. If the highest index found exceeds a specified similarity threshold, it is clear proof that the microbe species that belongs to the corresponding reference spectrum is present. There are special similarity thresholds for the assignment to families, genera or species.

It must be emphasized here that the mass spectrometric method has so far been mainly used for the identification of unknown microbes. Microbial isolates from well-separated colonies on agar plates have usually been used for the sample preparation. The identification of two, or at most three, species of microbe in a mixture of these two or three species has also been disclosed in U.S. Published Application 20100248298. One of the strengths of the mass spectrometric method that has not been utilized so far is its ability, under certain circumstances, to also detect the presence or absence of a species of target microbes in somewhat more complex mixtures of five, ten or more species of microbe unambiguously and with certainty.

SUMMARY OF THE INVENTION

Several cultivation steps for the target microbes are combined, preferably one or two cultivation steps, with a mass spectrometric detection of the target microbes in spectra of mixtures. The number of cultivation steps can thereby be considerably smaller than in current standard methods.

The mass spectrometric detection detects the presence or absence of the target microbes in the spectra of mixtures, even when the microbes account for a small proportion of the mixture. An unequivocal and certain detection is usually achieved even if the mixture spectrum is so complex that a mass spectrometric identification of the microbe species involved is no longer possible by similarity analyses using reference spectra.

It may be necessary to initially use a non-selective pre-cultivation in order to also reactivate damaged or greatly weakened target microbes if success is not guaranteed in selective nutrient media. Particularly advantageous, however, is preferential cultivation of the target microbes in a known way by selectively acting cultivation liquids, which usually contain inhibitors against foreign microbes that have the ability to multiply in high numbers. In many cases the inhibitors can be suitable metal salts, or antibiotics to which the target microbes are resistant. Selective nutrient media are known for a number of microbes; for others they must be specially developed. Selective nutrient media for *Salmonella*, for example, can positively influence the growth of the *Salmonella* as compared to *Escherichia* by more than a factor of 100, the antibiotic novobiocin being used in some of these nutrient media to inhibit the growth of *Escherichia*.

Particularly interesting target microbes are those microbe strains within a microbe species that are resistant to certain antibiotics. The target microbes here thus do not encompass all the microbes of a species, but only the resistant strains. They may be selectively cultivated in nutrient media that contain the appropriate antibiotics. Thus a specially developed nutrient medium containing various antibiotics may be used to develop a relatively fast detection method for multi-resistant *Staphylococcus aureus* (MRSA) that employs mass spectrometry after only one cultivation step.

With all these detection methods, the cultivation must be carried out in such a way that a multiplication of even one single target microbe in the sample leads to so many individual target microbes in the culture that these are sufficient for a mass spectrometric identification. This usually means around $10^5$ target microbes. The growth rates of the target microbes in the culture media must therefore be known.

A quantity of liquid taken from the culture liquid is centrifuged; the target microbes of the pellet are washed and digested in the centrifuge tube. The dissolved proteins are transferred to MALDI sample supports and measured mass spectrometrically. In the mass spectra acquired with sufficient sensitivity, the presence or absence of the target microbes may be recognized directly with suitable evaluation programs. Only if the complexity of the mass spectrum becomes too great does a further cultivation stage in a selective medium become necessary. The complexity can be determined from the mixture spectrum itself by determining, for example, what percentage of the mass spectrum is covered by mass signals. If this empty space in the mixture mass spectra is too small, a further selective cultivation must be carried out which improves the ratio of the target microbes to the foreign microbes.

These and other objects, features and advantages of the present invention will become more apparent in light of the following detailed description of preferred embodiments thereof, as illustrated in the accompanying figures.

BRIEF DESCRIPTION OF THE DRAWING

The FIGURE illustrates a method of mass spectrophotometric detection of microbes.

DETAILED DESCRIPTION OF THE INVENTION

A detection method for target microbes in which just a small number cultivation periods, each of 24 hours duration at most, are performed, preferably in selective nutrient media, before using a mass spectrometric detection method that recognizes the target microbes in mixtures.

The FIGURE illustrates a method of mass spectrophotometric detection of microbes.

In this detection method for target microbes the cultivation is carried out in such a way that the presence of one single target microbe in the sample leads to so many individual target microbes being produced in the culture that these are sufficient for a mass spectrometric identification. At least around $10^5$ target microbes are usually required for this identification. The growth rates of the target microbes in the culture media must therefore be known in order to provide this quantity of target microbes. The growth rates can easily be determined with known methods, however.

For certain target microbes it may be necessary to initially use a non-selective pre-cultivation in order to also reactivate damaged or greatly weakened target microbes if direct success is not guaranteed in selective nutrient media. Buffered peptone water, for example, is suitable for such a pre-cultivation. In some cases, this pre-cultivation is the only cultivation method required to detect the presence or absence of the target microbes with certainty in conjunction with the evaluation methods. As a rule, however, it will have to be followed with a cultivation in a selective nutrient medium.

One of the strengths, in principle, of the mass spectrometric method is its ability to detect the presence of a species of target microbe in somewhat complex mixtures of five, ten or more species of microbe unambiguously and with certainty when only the signature of these target microbe is still recognizable in the mass spectrum of the mixture. It is not necessary, and often not possible, to identify all the microbes of the mixture. The absence of a species of target microbe may also be reliably identified if definitely expected signals of the target microbe species are missing in at least one location, but preferably in two or three locations, in the mixture spectrum. "Definitely expected signals" are deemed to be those signals in the mass spectrum of target microbes which occur every time, preferably with only relatively small variations in intensity, in frequently repeated measurements of the target microbe spectra in different mixtures.

To detect the presence of a microbe species with certainty, the definitely expected mass signals of a reference spectrum of the target microbes must be present in the mixture spectrum. If the mixture spectrum is populated everywhere with mass signals, however, the presence of target microbes can be illusory. The mixture spectrum must therefore be examined to see how likely such an illusion is. A rough estimate shall be made here for this purpose. A mass spectrum of proteins acquired in the linear mode of a time-of-flight mass spectrometer can have around 2,000 separate mass signals in the mass range from about 3,000 to 15,000 daltons. A single species of microbe provides between about 50 and 70 mass signals. If a mixture contains around 20 species of microbe in approximately equal proportions, then around 1,000 mass signals are present, when overlaps are taken account of in only a very rough way. Statistically, around half of the mass signals of the target microbes should therefore be visible and not obscured. But if all mass signals of the target microbes are present in the mixture, possibly even with roughly the right intensities, there is a high probability that the target microbe species is present in the sample. Thus if the mixture spectrum has around 50 percent (or more) of free space, there is a high probability that a detection of the presence is correct.

Several conditions must be fulfilled for this detection method. First, the ionization process (MALDI) must be controlled in such a way that the proteins of the mixture are involved in the ionization with certainty. It must be ensured that individual proteins that have a low proton affinity do not fail to appear in the mass spectrum because their appearance is prevented by other components of the mixture. Second, the spectra must be carefully acquired, with better mass resolution and more precise reproducibility than is usually the case today, possibly even in a larger mass range. Third, special evaluation programs must be used that are able to detect the presence or absence of target microbes unambiguously and with certainty even if the target microbes amount to only between one and ten percent of the mixture, depending on the complexity of the mixture. The evaluation programs commercially available so far are not designed for this task; on the contrary they prevent this detection in favor of a reliable identification of microbes with the aid of clean microbe spectra.

Since these conditions were not given so far, this type of fast (and low-cost) detection of a target microbe species in mixtures has not been used in the prior art.

Ionization by MALDI is not uniform if many types of analyte substances, i.e., here, proteins of the various microbes in the mixture, are present. In the ionization process, the analyte substances compete for the available protons, and the substances with the highest proton affinities win. There are substances with a high proton affinity that can practically extinguish other ion signals. Sufficient protons are required to be made available.

First, one has to ensure that all the proteins of the mixture are ionized with roughly the same probability, if possible. This is often not the case with current acquisition techniques. In the region where the laser light is focused on the sample, the "laser spot", a plasma including heated and vaporized matrix substance forms with every laser shot. In this plasma, as in any hot plasma, some of the molecules of the matrix substance are ionized. The matrix substances are selected in such a way that their ions may donate protons to the much larger protein molecules, which have a higher proton affinity. If the energy density in the laser spot is low, resulting in only a moderately hot plasma being formed, then there will be too few proton donors to ionize all the protein molecules; a competitive situation develops which favors some proteins and disadvantages others. Investigations can be found in the literature that show that the number of ions in the plasma increases with the sixth or even seventh power of the energy density. However, if the energy density is simply increased while using the usual sizes of the laser spots, so many ions are formed in each laser shot that the ion detector goes into saturation for a large number of ion signals in an individual spectrum. It is not possible to produce a good mass spectrum in this way, especially as many of the signals that have gone into saturation become so wide that one can no longer decide whether it hides a signal of one single ionic species or maybe signals of two, three or four ionic species. There is therefore a dilemma between avoiding saturation on the one hand and the uniform ionization of all proteins on the other.

Modern laser systems such as Bruker's "Smart Beam" system can effect an improvement here, even if they cannot provide a complete remedy. At every shot, these laser systems can generate either one or more laser spots with a small diameter; and because of the small area, only a limited number of ions are delivered, even at high energy density in the laser spot. The duration of the laser light pulses is also optimized to provide the highest ion yield. The laser light pulses vaporize little material; the ionization yield is high, and the probability that molecules with low proton affinity will also become ionized is good. But even here, under optimum ionization conditions for microbe analysis, a large number of signals still go into saturation.

In this case it is helpful to acquire mass spectra of the microbe mixture with gradual increase of the energy density, and at high energy density to replace the saturated signals by extrapolations of unsaturated signals from spectra at lower energy density. This acquisition technique is not trivial due to the non-linear increase in the number of ions in response to the energy density, but it will not be explained in more detail here. It is thus possible to obtain mass spectra of the microbe mixture that are well resolved according to the ion masses, although many ion signals, often large parts of the mass spectrum, are already far into saturation at the highest energy density used. At this highest energy density, however, those proteins with low proton affinity are also ionized, so these proteins also become visible in their mass spectra.

The ions sometimes receive different initial accelerations because the processes in the ionization plasma are not fully reproducible. Consequently, not all the individual spectra are immediately summed to form a sum spectrum. It has become apparent that these conditions occasionally change sharply. It is therefore usual to initially sum small series comprising small numbers of individual mass spectra, about 20 to 50, for example. The quality of these small series of spectra, for example their mass resolution, is examined. If their quality is bad, they are rejected; if the quality is good, their mass scale is adjusted to that of the sum spectrum so far, and only then are they added to it. This procedure has proved to be successful, but must be adapted to the step-wise acquisition with increasing energy density.

Until now, the mass range from about 3,000 to 15,000 daltons has been used for the evaluation of the microbes because it had the largest information density for the identification. For identifying the presence or absence of target microbes in a mixture, however, it is advantageous if the mass spectrum contains large stretches without signals. It is therefore advantageous to extend the mass range used for the identification to around 20,000 daltons or even higher. Since this method only requires that the mass spectrum of the target microbes is known, and the reference spectra from reference libraries do not have to be used, this extension of the mass range is possible without having to create new reference libraries.

Optimum adjustment of the ion detector is required. A method for optimum adjustment is presented in U.S. Published Patent Application 20090206247, which is incorporated by reference. Moreover, it is advantageous to also suppress the electronic noise.

The evaluation program for the identification of a target microbe spectrum in mixture spectra must have a different structure to the current programs for similarity analysis. For a positive result the program checks whether all the definitely expected mass signals of the target microbe spectrum are present in the mixture spectrum; and for a negative result, whether those mass signals that definitely should be present are not present in empty stretches of the mixture spectrum. Whether a mass signal must definitely be present can be determined during the acquisition of the reference spectrum for this target microbe, for example by multiply repeated scans with determination of the variance of the intensities of the ion signals and repetition of these measurements with series of dilutions. Experience has shown there will be ion signals that are always present even at low concentrations, and conversely ion signals that are sometimes absent even at higher concentration.

With such a specially developed evaluation program is it possible to identify the presence or absence of target microbes. As described above, however, it is necessary to ensure that sufficient target microbes may have grown if only a single target microbe had been present in the sample.

Below is an example for a detection method according to an aspect of the present invention as used in the detection of Salmonella in food.

To detect Salmonella in food, about 10 to 25 grams of the coarsely cut-up food are incubated in about 225 ml of buffered peptone water for about 20 hours at around 37° Celsius. If the quantity of secondary flora in the material under analysis is small, Salmonella may be detected directly from this pre-enrichment culture by mass spectrometric analysis. This is done by taking about one milliliter of the pre-culture and centrifuging it for about two minutes at around 13,000 revolutions per minute in the microcentrifuge. The supernatant is discarded, and the pellet resuspended in about one milliliter of about 70 percent ethanol and centrifuged under the same conditions. After the supernatant has been discarded, the pellet is dried. The pellet is now lysed in about 20 to 50 microliters of about 70 percent formic acid, depending on its size, and then the same amount of acetonitrile is added. Insoluble cell components are separated by centrifuging for about two minutes in the microcentrifuge. Approximately one microliter of the lysate is pipetted onto a MALDI sample support. After drying, the sample is coated with around one microliter of HCCA solution. The HCCA solution contains about 10 milligrams of α-cyano-4-hydroxycinnamic acid per milliliter of solution, which includes about 50% acetonitrile, 2.5% trifluoroacetic acid and 47.5% water. HCCA serves as the matrix for the subsequent ionization of the proteins by matrix-assisted laser desorption.

As described above, the mass spectra are acquired with ionization by MALDI using small laser spots on the sample. The laser spots should have diameters of less than about 20 micrometers, preferably even less than about 10 micrometers, in order to achieve a high energy density and supply only a moderate number of ions. Furthermore, a step-wise acquisition of mass spectra with energy densities increased step-by-step is advantageous; regions of the mass spectra that are in saturation are replaced by extrapolation from mass spectra that have been acquired with lower energy density.

The food samples are not usually contaminated with several species of microbe (except when contaminated with feces). In these cases the evaluation programs detect whether Salmonella is present or not directly from the mass spectra obtained from the pre-culture.

A selective main enrichment step for Salmonella only needs to be carried out when there is strong secondary flora, which is visible in the mass spectrum of the microbe mixture and is detected by the evaluation program. This main enrichment step is necessary if, for example, less than about 50 percent of the mixture spectrum is free of mass signals. Depending on the required degree of certainty of the detection, it is also possible to stipulate here that only about 30 percent, or better about 70 percent, of the mass spectrum must be free of mass signals.

The main enrichment step involves transferring about one milliliter into MKTTn broth or about 0.1 milliliter into RVS broth and incubating it for about 24 hours at around 37° Celsius. Approximately half a milliliter is then taken from the culture and prepared as described above as mass spectrometric MALDI samples. From the mass spectra of a digestion of the microbes of this second cultivation step, the presence or absence of Salmonella in the food sample may then be determined unequivocally. The detection of Salmonella in food here usually takes one, at most two, days instead of the four to five days required for conventional methods.

To detect other microbes, or microbes in other types of sample, the detection method is easily adapted in each case using selective nutrient media.

As was described above, mass spectra of the microbe digestions are preferably acquired with an ionization by MALDI in time-of-flight mass spectrometers that are especially equipped for this. Ionization by MALDI has the advantage that essentially only singly charged ions of the proteins are generated; this means that the mass spectrum is drawn out over a wide range of the charge-related masses m/z, and can be evaluated simply and effectively. Ionization by other methods, such as electrospray ionization (ESI), and also the use of other mass spectrometers shall not be excluded here, however.

Although the present invention has been illustrated and described with respect to several preferred embodiments thereof, various changes, omissions and additions to the form and detail thereof, may be made therein, without departing from the spirit and scope of the invention.

What is claimed is:

1. A method of determining the absence of target microbes in a sample using mass spectrometry, comprising:
    determining definitely expected mass signals of the target microbes during acquisition of reference spectra for the target microbes, including multiply repeated scans from the target microbes with determination of a variance of ion signal intensities and repetition of such measurements using series of dilutions, wherein the definitely expected mass signals are those signals of the target microbes which occur every time in said multiply repeated scans;
    recording the definitely expected mass signals in an evaluation program configured to determine whether the definitely expected mass signals are missing from predetermined spectrum locations;
    cultivating microbes of the sample in a liquid nutrient medium selective for the target microbes;
    applying the cultivated microbes to a sample support of a mass spectrometer which uses matrix assisted laser desorption ionization (MALDI) as an ionization process;
    operating the mass spectrometer to acquire a mixture mass spectrum of the cultivated microbes; and
    analyzing the mixture mass spectrum with the evaluation program and indicating the absence of the target microbes in the sample, when one of the definitely expected mass signals of the target microbes is not present in the mixture mass spectrum.

2. The method of claim 1, wherein the step of cultivating is prepared in such a way that at least about 100,000 target microbes can grow from one target microbe in the sample.

3. The method of claim 1, wherein microbial proteins are ionized by pulses of laser light from a pulsed UV laser, the laser light being focused to a laser spot on the sample under analysis.

4. The method of claim 3, wherein the laser spot on the sample under analysis has a diameter of less than about 20 micrometers.

5. The method of claim 1, wherein the selective nutrient medium comprises metal salts and/or antibiotics to which the target microbes are resistant.

6. The method of claim 1, wherein the target microbes are those strains within a microbe species that are resistant to certain antibiotics and the selective nutrient medium comprises appropriate antibiotics.

7. The method of claim 6, wherein the target microbes are a multi-resistant *Staphylococcus aureus*.

8. The method of claim 1, wherein the target microbes are *Salmonella* and the selective nutrient medium comprises the antibiotic novobiocin.

9. The method of claim 1, wherein the step of acquiring comprises ionizing soluble microbe proteins of the cultivated microbe.

10. The method of claim 9, wherein several mixture mass spectra of the cultivated microbes, each with increased energy density in a laser spot, are acquired from one analytical sample, and regions of the mixture mass spectrum that exhibit a saturation of the ion detector are replaced by spectral regions whose intensity has been extrapolated from mixture mass spectra which have been acquired at lower energy density and are not in saturation.

11. A method of determining the absence of target microbes in a sample using mass spectrometry, comprising:
(a) determining definitely expected mass signals of the target microbes during acquisition of reference spectra for the target microbes, including multiply repeated scans from the target microbes with determination of a variance of ion signal intensities and repetition of such measurements using series of dilutions, wherein the definitely expected mass signals are those signals in a reference mass spectrum of the target microbes which occur every time in saki multiply repeated scans;
(b) recording the definitely expected mass signals in an evaluation program configured to determine whether the definitely expected mass signals are missing from predetermined spectrum locations;
(c) cultivating microbes of the sample in a non-selective liquid nutrient medium;
(d1) applying the cultivated microbes to a sample support of a mass spectrometer which uses matrix assisted laser desorption ionization (MALDI) as an ionization process;
(d2) operating the mass spectrometer to acquire a first mixture mass spectrum of the cultivated microbes;
(e) determining an empty space in the first mixture mass spectrum which is not covered by mass signals;
(f1) analyzing the mixture mass spectrum with the evaluation program and, if the first mixture mass spectrum is not too densely populated with mass signals, indicating the absence of the target microbes in the sample, when one of the definitely expected mass signals of a reference mass spectrum of the target microbes is not present in the first mixture mass spectrum; and
(f2) if the first mixture mass spectrum is too densely populated with mass signals, further cultivating the microbes cultivated in step (c) in a liquid nutrient medium selective for the target microbes, acquiring a second mixture mass spectrum of the microbes cultivated in the selective nutrient medium, analyzing the mixture mass spectrum with the evaluation program and indicating the absence of the target microbes in the sample, when one of the definitely expected mass signals of the target microbes is not present in the second mixture mass spectrum.

12. The method of claim 11, wherein the first mixture mass spectrum is considered too densely populated with mass signals if more than about 50 percent of the first mixture mass spectrum is populated by mass signals.

13. The method of claim 11, wherein the selective nutrient medium in step (f2) comprises metal salts and/or antibiotics to which the target microbes are resistant.

14. The method of claim 11, wherein the target microbes are those strains within a microbe species that are resistant to certain antibiotics and the selective nutrient medium comprises appropriate antibiotics.

15. The method of claim 14, wherein the target microbes are a multi-resistant *Staphylococcus aureus* (MRSA).

16. The method of claim 11, wherein the target microbes are *Salmonella* and the selective nutrient medium comprises the antibiotic novobiocin.

17. A method of determining the absence of target microbes resistant to an antibiotic using mass spectrometry, comprising:
determining definitely expected mass signals of the target microbes during acquisition of reference spectra for the target microbes, including multiply repeated scans from the target microbes with determination of a variance of ion signal intensities and repetition of such measurements using series of dilutions, wherein the definitely expected mass signals are those signals of the target microbes which occur every time in said multiply repeated scans;
recording the definitely expected mass signals in an evaluation program configured to determine whether the definitely expected mass signals are missing from predetermined spectrum locations;
cultivating microbes of the sample in a liquid nutrient medium comprising the antibiotic;
acquiring by matrix assisted laser desorption (MALDI) a mixture mass spectrum of the cultivated microbes; and
analyzing the mixture mass spectrum with the evaluation program and indicating the absence of resistant target microbes in the sample, when one of the definitely expected mass signals of the target microbes is not present in the mixture mass spectrum.

* * * * *